United States Patent [19]

Maleski

[11] Patent Number: 5,663,434

[45] Date of Patent: Sep. 2, 1997

[54] PROCESS FOR PREPARING N-(3-AMINO-4-CHLOROPHENYL) ACYLAMIDES

[75] Inventor: Robert Joseph Maleski, Kingsport, Tenn.

[73] Assignee: Eastman Chemical Company, Kingsport, Tenn.

[21] Appl. No.: 593,726

[22] Filed: Jan. 29, 1996

[51] Int. Cl.⁶ .................... C07C 231/02; C07C 303/38
[52] U.S. Cl. .................... 564/92; 548/368.4; 548/368.7; 564/99; 564/142; 564/155; 564/175
[58] Field of Search ............... 564/92, 99, 142, 564/155, 158, 175; 548/368.4, 368.7

[56] References Cited

U.S. PATENT DOCUMENTS

| | | | |
|---|---|---|---|
| 3,265,506 | 8/1966 | Weissberger et al. | 96/100 |
| 3,408,194 | 10/1968 | Loria | 96/100 |
| 3,894,875 | 7/1975 | Cameron et al. | 96/100 |
| 3,920,710 | 11/1975 | Kalopisses et al. | 564/92 |
| 4,283,556 | 8/1981 | Lang | 564/144 |
| 4,448,719 | 5/1984 | Schwander | 260/152 |
| 4,540,815 | 9/1985 | Papenfuhs et al. | 564/216 |
| 5,008,179 | 4/1991 | Chari et al. | 430/546 |

*Primary Examiner*—Peter O'Sullivan
*Attorney, Agent, or Firm*—Karen A. Harding; Harry J. Gwinnell

[57] ABSTRACT

The present invention provides a process for preparing N-(3-amino-4-chlorophenyl) acylamides of Formula I:

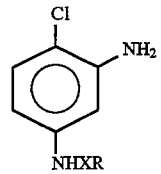

comprising reacting, in a solvent comprising at least one polar solvent, in the presence of at least one acid acceptor, 1-chloro-2,4-diaminobenzene with at least one acyl chloride of formula I:

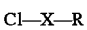

wherein X is —CO— or —SO$_2$—; R is selected from the group C$_1$–C$_{25}$ alkyl; C$_1$–C$_{25}$ alkyl substituted with one or more groups selected from C$_1$–C$_{12}$ alkoxy, aryl, aryloxy and C$_5$–C$_7$ cycloalkyl; aryl; C$_5$–C$_7$ cycloalkyl. The present invention further comprises the step of purifying said N-(3-amino-4-chlorophenyl) acylamides by crystallizing from a non-polar solvent or conducting the reaction in a mixture of at least one polar and at least one non-polar solvent.

20 Claims, No Drawings

PROCESS FOR PREPARING N-(3-AMINO-4-CHLOROPHENYL) ACYLAMIDES

INTRODUCTION

This invention relates to an improved process for preparing N-(3-amino-4-chlorophenyl) acylamides which are useful as intermediates for couplers for preparing disperse azo dyes for dyeing textile fibers and for preparing couplers which are useful in color photography. The process involves the selective acylation of the 4-amino group in 1-chloro-2,4-diaminobenzene using certain acyl chlorides in the presence of an acid acceptor.

PRIOR ART

U.S. Pat. No. 4,448,719 (Example 28) teaches the selective acylation of 1-chloro-2,4-diaminobenzene using 2-methoxyethyl chlorocarbonate in a reaction mixture of chlorobenzene and water. No yields are given. The use of the reaction conditions of this method to produce the N-(3-amino-4-chlorophenyl) acylamides of this invention gives very low yields of product (see Comparative Example 1).

U.S. Pat. No. 4,283,556 teaches the selective mono acylation of 1-methoxy-2,4-diaminobenzene using anhydrides in alcohols as solvents. Using anhydrides to introduce the acyl group is inherently less efficient than acylation with acyl halides, since approximately one half of the weight of anhydride is lost during the reaction in the form of the corresponding acid. This is particularly disadvantageous in preparing the intermediates for photographic couplers, since the acylating agent is usually used to introduce a complicated and expensive ballast group into the coupler. Similarly, U.S. Pat. No. 4,540,815 describes the selective acylation of 1,3-diaminobenzene and 1-$C_1$-$C_4$ alkoxy-2,4-diaminobenzenes using anhydrides in the presence of $C_1$-$C_4$ alkanols and hydrogen halides to precipitate the monoacylated compounds when formed to prevent further acylation.

DETAILED DESCRIPTION OF THE INVENTION

This invention relates to a process for preparing N-(3-amino-4-chlorophenyl) acylamides of Formula I:

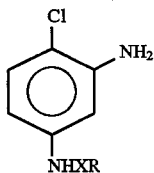

comprising reacting, in a solvent comprising at least one polar solvent, in the presence of an acid acceptor, 1-chloro-2,4-diaminobenzene with at least one acyl chloride of formula II:

Cl—X—R wherein x is —CO— or —$SO_2$—; R is selected from the group $C_1$-$C_{25}$ alkyl; $C_1$-$C_{25}$ alkyl substituted with one or more groups selected from $C_1$-$C_{12}$ alkoxy, aryl, aryloxy and $C_5$-$C_7$ cycloalkyl; aryl; $C_5$-$C_7$ cycloalkyl. The N-(3-amino-4-chlorophenyl) acylamides I, are useful as intermediates for producing disperse textile dyes and couplers for color photography. The reaction of 1-chloro-2,4-diaminobenzene with acyl chlorides II is as follows:

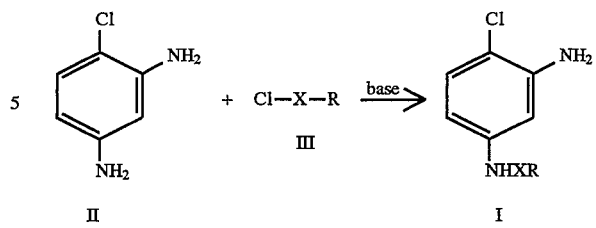

wherein X and R are as defined above.

It has been discovered that high yields of useful compounds I having high purity are obtained by reacting the 1-chloro-2,4-diaminobenzene II with acyl chlorides III as described above in certain polar solvents. If the reaction is conducted in a polar solvent the purification is generally conducted in a non-polar solvent. Preferably mixtures of certain nonpolar solvents and certain polar solvents present at up to about 50% by weight are used. The nonpolar solvent is selected from $C_5$-$C_7$ alkanes, benzene, toluene, ethylbenzene, cumene and xylenes, or mixtures thereof, with toluene being preferred. Useful polar solvents include $C_1$-$C_3$ alkanols, with methanol being preferred. Preferably, the solvent mixture contains from about 20 to about 50% by weight of the polar solvent.

The mixed solvents as described above are particularly useful for promoting the completion of the acylation reaction and further for removing any bis acylated product, which may occur as an undesired impurity, during isolation of the desired product.

The monoacylation reactions are carried out in the presence of one or more acid acceptors, usually selected from tertiary amines, e.g. triethylamine, tri-n-butylamine, $N,N^1$-dialkylpiperazines and $N,N,N^1,N^1$-tetraalkylethylenediamines; N,N-dialkylanilines, e.g. N,N-dimethylanilines; nitrogen containing heterocyclic compounds, e.g. pyridine, picolines, lutidines, quinolines, isoquinolines, pyrroles, imidazoles and mixtures thereof. Preferred acid acceptors are triethylamine, pyridine, picolines, lutidines, imidazole and mixtures thereof.

The acylation reaction is usually carried out at temperatures ranging from about −15° to about +75° C., preferably from about −5° to about +50° C.

Prior to the present invention the N-(3-amino-4-chlorophenyl) acylamides were made from chloro nitro anilines via a difficult multi step process (e.g. as disclosed in U.S. Pat. No. 3,265,506, Example 8). The selective acylation of 1-chloro-2,4-diaminobenzene according to the process of this invention provides an alternative process which offers high yields of desired products having excellent purity. Since the starting 1-chloro-2,4-diaminobenzene for this method is derived by reduction of 1-chloro-2,4-dinitrobenzene, which is readily available and cheap, the method offers improved economics versus previously disclosed methods.

The terms "aryl" and "aryloxy" are used to denote aromatic monovalent radicals selected from the classes of benzene and naphthalene and these radicals substituted with one or more groups selected from $C_1$-$C_{25}$ alkyl; $C_1$-$C_{12}$ alkoxy; hydroxy; nitro; halogen; $C_5$-$C_7$ cycloalkyl; $C_1$-$C_{12}$ alkanoyloxy; $C_1$-$C_{12}$ alkanoylamino; $C_1$-$C_{12}$ alkanesulfonamido; phenylsulfonyl and phenylsulfonyl substituted by one or more groups selected from $C_1$-$C_{12}$ alkoxy, $C_1$-$C_{12}$ alkanoyloxy, benzyloxy, $OR_1$, and $OCOR_1$, wherein $R_1$ is phenyl or phenyl substituted by $C_1$-$C_{12}$ alkyl, $C_1$-$C_{12}$ alkoxy or halogen.

The term $C_1$-$C_{25}$ alkyl is used to denote a straight or branched chain hydrocarbon radical having 1 to 25 carbons.

In the terms "$C_1$-$C_{12}$ alkoxy", "$C_1$-$C_{12}$ alkanoyloxy", "$C_1$-$C_{12}$ alkanoylamino" and "$C_1$-$C_{12}$ alkanesulfonamido", the alkyl portion of the group is a straight or branched chain hydrocarbon moiety containing 1 to 12 carbon atoms.

The term "halogen" is used to include fluorine, chlorine, bromine and iodine.

In a preferred embodiment of the invention, X is —CO—, and R is preferably $C_1$-$C_{20}$ alkyl substituted with a phenoxy radical containing one or more groups selected from $C_1$-$C_{20}$ alkyl, hydroxy, nitro, $C_1$-$C_{12}$ alkanesulfonamido, $C_1$-$C_{12}$ alkanoyloxy and halogen. In another preferred embodiment, X is CO and R is phenyl or phenyl substituted with $C_1$-$C_{20}$ alkyl, $C_1$-$C_{12}$ alkoxy or nitro. In another preferred embodiment of the invention, X is —$SO_2$— and R is a $C_1$-$C_{20}$ alkyl radical. Typical acyl chlorides III which are useful in the practice of the invention are provided in Table I.

The N-(3-amino-4-chlorophenyl) acylamides of Formula I may be readily converted to provide useful derivatives IV.

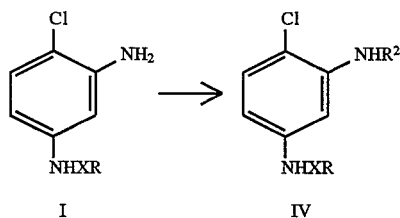

The above reaction may be conducted via a number of methods which are generally known in the art.

The class of compounds within Formula IV wherein X is CO; R is $C_1$-$C_4$ alkyl, substituted $C_1$-$C_4$ alkyl or aryl; $R^2$ is hydrogen unsubstituted or substituted $C_1$-$C_8$ alkyl, or unsubstituted or substituted $C_3$-$C_4$ alkenyl are known to be useful as couplers for producing azo disperse dyes for textile fibers (U.S. Pat. No. 4,448,719; Dyes and Pigments 4 (1983) 195–211).

The class of compounds within Formula IV wherein X is —CO— and —$SO_2$—; R is $C_1$-$C_{25}$ alkyl, substituted $C_1$-$C_{25}$ alkyl or aryl; $R^2$ an active methylene moiety such as 1-aryl-5-pyrazolone-3-yl or pivaloyl are useful intermediates for color photography [U.S. Pat. No. 5,008,179 (See Columns 7,8,9); U.S. Pat. No. 3,265,506 (See Columns 5,7,8); U.S. Pat. No. 3,894,875 (See Columns 4,5,6,7,8); U.S. Pat. No. 3,408,194 (See Column 6)].

The following examples illustrate further the practice of the invention.

EXAMPLE 1

A room temperature solution of 1-chloro-2,4-diaminobenzene (1.43 g, 10 mmol), 1-hexadecanesulfonyl chloride (3.24 g, 10 mmol), imidazole (0.68 g, 10 mmol) and toluene (20 mL) was stirred for 1 hr. Isopropyl alcohol (20 mL) was added and the reaction mixture was heated at 60° C. for 2 hours. Analysis by thin layer chromatography (tlc) (40% ethyl acetate and 60% heptane) indicated incomplete acylation and additional 1-hexadecanesulfonyl chloride (0.7 g, 2 mmol) was added and the reaction mixture was stirred at 60°–62° C. for an additional hour, at which time the reaction appeared to be complete by tlc analysis. The reaction solution was treated with hot water (50 mL) and the layers separated. The toluene layer was further washed twice with 50 mL of hot water. Heptane (20 mL) was added to the recovered toluene layer to precipitate the product, N-(3-amino-4-chlorophenyl)-1-hexadecanesulfonamide, which was isolated by cooling the mixture to about 0° C. and collecting the product by vacuum filtration. After being washed with cold heptane, the product was dried (yield=3.12 g, 72% of the theoretical yield) and it melted at 103°–104° C. No impurities were observed by $H^1NMR$ analysis.

EXAMPLE 2

A solution of 1-chloro-2,4-diaminobenzene (1.43 g, 0.01 mole) and triethyl amine (1.1 g, 0.011 mole) in a mixture of methyl alcohol (5.0 mL) and toluene (10.0 mL) was stirred and cooled to about −5° C. To this solution was added 4-(2,4-di-tert-pentylphenoxy)butyryl chloride (3.60 g, 0.0107 m) at less than +5° C. The reaction mixture was stirred overnight and allowed to warm to room temperature. The mixture was examined via HPLC and found to be 87% desired product and 10% of the undesired bis-acylated compound. The methanol and hydrochloride salt of the amine were removed by washing the toluene layer with water. After evaporating the toluene layer to dryness the crude product was recrystallized from a solution of 10 mL of heptane and 5 mL of toluene. The yield of solid product was 4.10 g. High pressure liquid chromatography, analysis (HPLC) indicated that the crude product consisted of 98.4% by weight (90.7% of the theoretical yield) of the desired monoacylated product N-(3'-amino-4'-chlorophenyl)-4-(2,4-di-tert-pentylphenoxy)butyramide shown below,

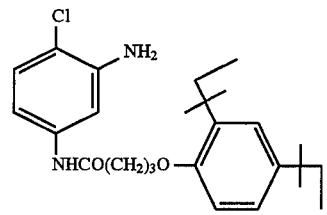

0.1% by weight of the starting 1-chloro-2,4-diaminobenzene and 0.6% by weight of the his acylated product. None of the isomeric product resulting from acylation of the 2-amino group of the starting material was observed.

EXAMPLE 3

Example 2 was repeated using lutidine(1.2 g, 0.011 mol) as the acid acceptor to yield 3.38 g of product which by HPLC was shown to consist of 96.8% by weight (73.5% of the theoretical yield) of the desired monoacylated product, 0.65% by weight of starting 1-chloro-2,4-diaminobenzene and 0.9% by weight of the bis acylated product.

EXAMPLE 4

A solution of 1-chloro-2,4-diaminobenzene (1.43 g, 0.01 mol) and imidazole (0.7 g) in a mixture of toluene (10.0 mL) and methyl alcohol (5.0 mL) was stirred and treated with benzoyl chloride at 0°–5° C. The reaction mixture was stirred at 0°–5° C. for 1 hour and then allowed to stir overnight at room temperature. Water (20 mL) and ethyl acetate (30 mL) were added and the mixture was then heated until all of the solid had dissolved. The water layer was separated and the organic layer was evaporated to dryness. After recrystallization from toluene, 2.13 grams of product were obtained (86.3% of the theoretical yield). The product, which showed only one component present by thin layer chromatography and which melted at 160°–161° C., had the following structure:

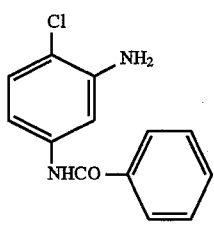

The product was high quality by H¹ NMR.

EXAMPLE 5

A solution of 1-chloro-2,4-diaminobenzene (1.43 g, 0.01 mol) and imidazole (0.0113 mol) in toluene (10.0 mL) and methyl alcohol (5.0 mL) was stirred and treated at 0°–5° C. with a solution of p-toluene sulfonyl chloride (2.1 g, 0.0108 mol) in toluene (10.0 mL). The reaction mixture was stirred overnight at room temperature and then washed with water (40.0 mL). The aqueous layer was discarded and the solvent was removed from the organic layer by evaporation. After recrystallization of the residue from a mixture of toluene-ethyl acetate, the product was obtained in 88.3% yield by weight. By H¹ NMR, the product was 97.2% pure by weight and had the following structure:

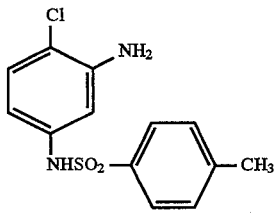

Thus, an actual yield of 85.8% of the theoretical yield was obtained.

COMPARATIVE EXAMPLES 1 (U.S. Pat. No. 4,448,719, Ex. 28)

A mixture of 1-chloro-2,4-diaminobenzene (4.27 g, 0.03 mol), chlorobenzene (15 mL) and water (15 mL) was stirred vigorously and treated with a solution of 4-(2,4-di-tert-pentylphenoxy)butyryl chloride (0.03 mol) at 8°–10° C., while the pH was kept at 6–7 by the addition of a 5% by weight aqueous sodium carbonate solution. The reaction mixture was stirred for 0.5 hour and was examined by HPLC and found to be a mixture of 63% of the desired product and 30% of the undesired bis-acylated compound. The mixture was heated to about 70° C. to dissolve the solids present. The aqueous layer was separated off and the organic layer washed with hot water (50.0 mL). The solvent was removed under vacuum from the organic layer to yield a solid residue which was recrystallized from a mixture of heptane (30.0 mL) and toluene (15.0 mL) to yield 3.67 g (33.0% of the theoretical yield) of product which was high quality (by tlc) product having the following structure:

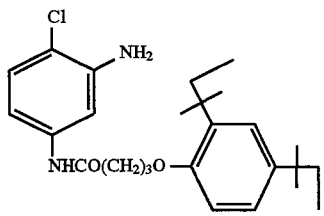

Compared to the procedure of this invention utilized in Example 2 above (90.7% of the theoretical yield, 87% desired product in the reaction mixture), a much lower yield of product was obtained using the reaction conditions of known process (33% of theoretical yield, 63% desired product in the reaction mixture). Thus, the process of the present invention is nearly three times more efficient than the prior art process.

TABLE I

Typical Acyl Halides

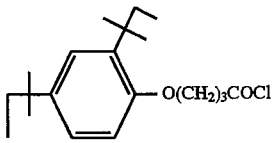
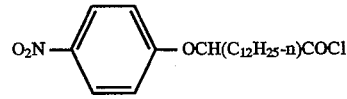
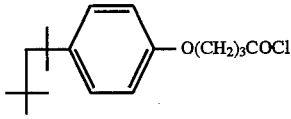
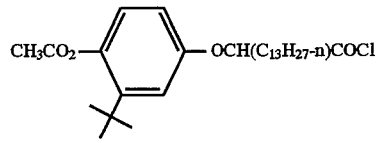
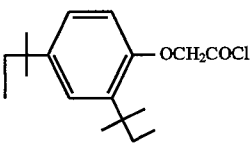
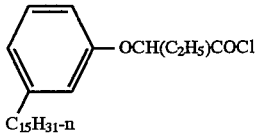
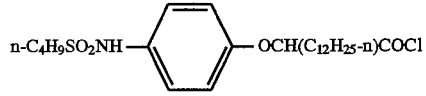

TABLE I-continued
Typical Acyl Halides
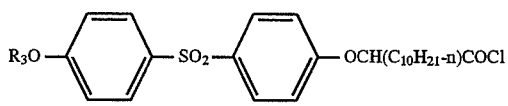 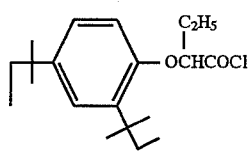
$R_3 = C_1-C_{12}$ alkyl, $C_1-C_{12}$ alkanoyloxy, benzyloxy, aryl or aroyloxy
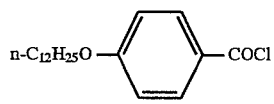     $CH_3COCl$
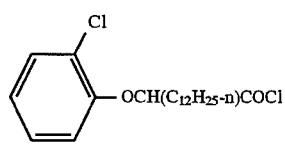     $(CH_3)_2CHCOCl$
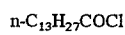 n-$C_{13}H_{27}COCl$     $CH_3(CH_2)_3CH(C_2H_5)COCl$
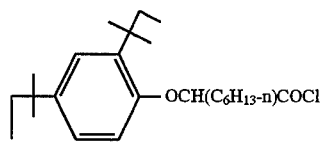     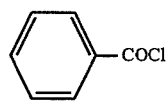
$CH_3SO_2Cl$    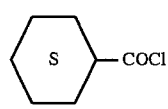
n-$C_4H_9SO_2Cl$    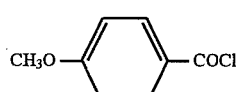
n-$C_{25}H_{51}SO_2Cl$    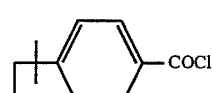
n-$C_{16}H_{33}SO_2Cl$    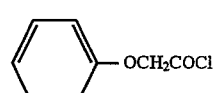
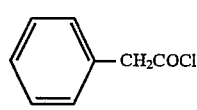     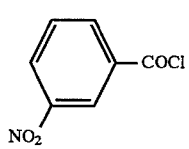
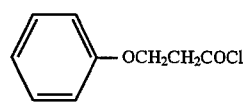
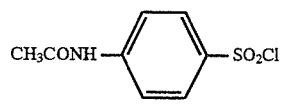     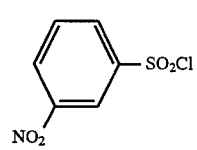

TABLE I-continued

Typical Acyl Halides

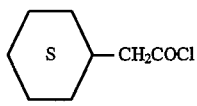

I claim:
1. A process for preparing N-(3-amino-4-chlorophenyl) acylamides of Formula I:

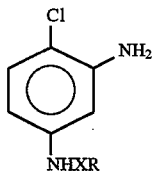

comprising reacting, in a solvent comprising at least one polar solvent selected from the group consisting of $C_1$–$C_3$ alkanols and mixtures thereof, in the presence of at least one acid acceptor, 1-chloro-2,4-diaminobenzene with at least one acyl chloride of formula I:

wherein X is —CO— or —SO$_2$—; R is selected from the group $C_1$–$C_{25}$ alkyl; $C_1$–$C_{25}$ alkyl substituted with one or more groups selected from $C_1$–$C_{12}$ alkoxy, aryl, aryloxy and $C_5$–$C_7$ cycloalkyl; aryl; $C_5$–$C_7$ cycloalkyl.

2. The process of claim 1 wherein said polar solvent comprises methanol.

3. The process of claim 1 wherein said solvent further comprises at least one non-polar solvent.

4. The process of claim 3 wherein said non-polar solvent comprises at least about 50% by weight of the solvent.

5. The process of claim 3 wherein said at least one non-polar solvent is selected from the group consisting of $C_5$–$C_7$ alkanes, benzene, toluene, ethylbenzene, cumene and xylenes, or mixtures thereof.

6. The process of claim 3 wherein said at least one non-polar solvent comprises toluene.

7. The process of claim 3 wherein said at least one non-polar solvent comprises between about 50 to about 80% by weight of the solvent.

8. The process of claim 1 wherein said acid acceptor is selected from the group consisting of tertiary amines, N,N,N$^1$,N$^1$-tetraalkylethylenediamines, N,N-dialkylanilines, N,N-dimethylanilines and nitrogen containing heterocyclic compounds and mixtures thereof.

9. The process of claim 8 wherein said acid acceptor is selected from the group consisting of triethylamine, tri-n-butylamine, N,N$^1$-dialkylpiperazines, pyridine, picolines, lutidines, quinolines, isoquinolines, pyrroles, imidazoles and mixtures therof.

10. The process of claim 9 wherein said acid acceptor is selected from the group consisting of triethylamine, pyridine, picolines, lutidines, imidazole and mixtures thereof.

11. The process of claim 1 wherein said reacting step is conducted at a temperature from about −15° to about +75° C.

12. The process of claim 11 wherein said temperature is between about −5° to about +50° C.

13. The process of claim 1 wherein X is —CO—, and R is $C_1$–$C_{20}$ alkyl substituted with a phenoxy radical containing one or more groups selected from $C_1$–$C_{20}$ alkyl, hydroxy, nitro, $C_1$–$C_{12}$ alkanesulfonamido, $C_1$–$C_{12}$ alkanoyloxy and halogen.

14. The process of claim 1 wherein X is CO and R is phenyl or phenyl substituted with $C_1$–$C_{20}$ alkyl, $C_1$–$C_{12}$ alkoxy or nitro.

15. The process of claim 1 wherein X is —SO$_2$— and R is $C_1$–$C_{20}$ alkyl.

16. The process of claim 1 futher comprising the step of reacting said N-(3-amino-4-chlorophenyl) acylamides to provide useful the compounds of Formula IV

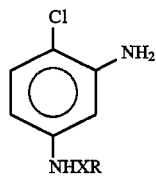

wherein R$^2$ is selected from hydrogen, unsubstituted or substituted $C_1$–$C_8$ alkyl and unsubstituted or substituted $C_3$–$C_4$ alkenyl.

17. The process of claim 16 wherein X is CO; R is $C_1$–$C_4$ alkyl, substituted $C_1$–$C_4$ alkyl or aryl; R$_2$ is hydrogen unsubstituted or substituted $C_1$–$C_8$ alkyl, or unsubstituted or substituted $C_3$–$C_4$ alkenyl.

18. The proces of claim 16 wherein X is —CO— and —SO$_2$—; R, is $C_1$–$C_{25}$ alkyl, substituted $C_1$–$C_{25}$ alkyl or aryl; R$_2$ is an active methylene moiety.

19. The process of claim 17 wherein said active methylene moiety is 1-aryl-5-pyrazolone-3-yl or pivaloyl.

20. The process of claim 1 futher comprising the step of purifying said N-(3-amino-4-chlorophenyl) acylamides by crystallizing from a non-polar solvent.

* * * * *

UNITED STATES PATENT AND TRADEMARK OFFICE
CERTIFICATE OF CORRECTION

PATENT NO. : 5,663,434
DATED : September 2, 1997
INVENTOR(S) : Robert Joseph Maleski It is certified that error appears in the above-identified patent and that said Letters Patent is hereby corrected as shown below:

Column 10, Claim 16, line 32, the formula should be

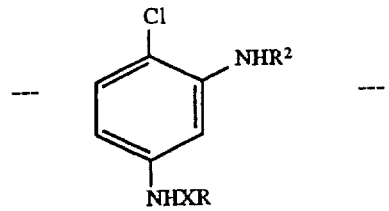

Signed and Sealed this

Fifteenth Day of May, 2001

Attest:

NICHOLAS P. GODICI

Attesting Officer

Acting Director of the United States Patent and Trademark Office